United States Patent
Park et al.

(10) Patent No.: US 9,226,905 B2
(45) Date of Patent: Jan. 5, 2016

(54) PHARMACEUTICAL COMPOSITION FOR PREVENTING OR TREATING MUSCLE WASTING-RELATED DISEASE COMPRISING DIAMINODIPHENYLSULFONE OR PHARMACEUTICALLY ACCEPTABLE SALT THEREOF

(71) Applicant: SAMSUNG ELECTRONICS CO., LTD., Suwon-si, Gyeonggi-do (KR)

(72) Inventors: Sang Chul Park, Gyeonggi-do (KR); Sung Chun Cho, Incheon (KR); Young Hoon Son, Seoul (KR); Sun Gun Chung, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/363,416

(22) PCT Filed: Dec. 7, 2012

(86) PCT No.: PCT/KR2012/010647
§ 371 (c)(1),
(2) Date: Jun. 6, 2014

(87) PCT Pub. No.: WO2013/085351
PCT Pub. Date: Jun. 13, 2013

(65) Prior Publication Data
US 2015/0031773 A1   Jan. 29, 2015

(30) Foreign Application Priority Data
Dec. 7, 2011   (KR) .................. 10-2011-0130607

(51) Int. Cl.
*A61K 31/145*   (2006.01)
*A23L 1/30*   (2006.01)
*A61K 31/136*   (2006.01)

(52) U.S. Cl.
CPC ............... *A61K 31/145* (2013.01); *A23L 1/30* (2013.01); *A61K 31/136* (2013.01); *A23V 2002/00* (2013.01)

(58) Field of Classification Search
CPC .............................. A61K 31/18; A61K 31/16
USPC .......................................... 514/646; 564/430
See application file for complete search history.

(56) References Cited

FOREIGN PATENT DOCUMENTS

| | | |
|---|---|---|
| CN | 101332187 A | 12/2008 |
| EP | 2 425 829 A1 | 7/2012 |
| JP | 2006528175 A1 | 1/2005 |
| JP | 2011513304 | 4/2011 |
| KR | 1020090061010 | 6/2009 |
| KR | 1020110049808 | 5/2011 |
| WO | 2010126349 A1 | 4/2010 |
| WO | 2010/126349 A1 | 11/2010 |

OTHER PUBLICATIONS

Massucatti et al. Disseminated granuloma annulare in a patient with type II diabetes mellitus: Sucessful treatment with dapsone. Medicina Cutanea Ibero-Latino-Americana, (Nov.-Dec. 2010) vol. 38, No. 6, pp. 241-243. abstract.*
Chinese Office Action cited in Application No. 201280060674.X issued May 29, 2015.
Epidemiology, 5th edition, Yilin Ma et al., Shanghai Science and Technology Press, May 2011, pp. 583-585, published on May 31, 2011.

* cited by examiner

*Primary Examiner* — Jennifer M Kim
(74) *Attorney, Agent, or Firm* — Leydig, Voit & Mayer, Ltd.

(57) ABSTRACT

The present invention relates to a pharmaceutical composition for preventing or treating a muscle wasting-related disease comprising diaminodiphenylsulfone (Dapsone; DDS) or a pharmaceutically acceptable salt thereof as an active ingredient. The composition according to the present invention may be effectively used to prevent or treat a muscle wasting-related disease by increasing muscle mass, preventing muscle loss and effectively restoring muscle function.

10 Claims, 9 Drawing Sheets

PHARMACEUTICAL COMPOSITION FOR PREVENTING OR TREATING MUSCLE WASTING-RELATED DISEASE COMPRISING DIAMINODIPHENYLSULFONE OR PHARMACEUTICALLY ACCEPTABLE SALT THEREOF

TECHNICAL FIELD

The present invention relates to a pharmaceutical composition comprising diaminodiphenylsulfone, which can be effectively used for the prevention or treatment of a muscle wasting-related disease.

BACKGROUND ART

The muscle mass in all people decreases by about 10-15% in 50-70 years of age and 30% or more in 70-80 years of age, resulting in decreases in muscle strength and function. This is called sarcopenia. Sarcopenia, a muscular disease that occurs in most elderly individuals, presents with the decrease in muscle mass with aging. When this senile sarcopenia is not treated, it causes a painful old age life due to a discomfort performance of physical function and can also cause various age-related diseases, including diabetes, obesity, cardiovascular diseases, osteoporosis and the like.

Various studies on the efficient control of sarcopenia have been conducted. It was found that treatment with, for example, growth hormone (GH), can increase muscle mass. However, this treatment is very expensive and cause some undesired side effects such as shortening average life expectancy. As one of the most efficient methods for delaying the progression of sarcopenia, exercise has been recommended, but it is very unsuitable for elderly or sickbed patients. Thus, there is an urgent need to develop a drug and technology for treating sarcopenia, which can induce the regeneration and differentiation of muscle.

Meanwhile, it was reported that diaminodiphenylsulfone (Dapsone; DDS) well-known as an antibiotic increases the life span of *Caenorhabditis elegans* by 20-30%. DDS is a substance synthesized one century ago, is well known as a therapeutic agent for leprosy and is used as an important drug for many other skin diseases.

DISCLOSURE

Technical Problem

However, the effect of DDS against muscle diseases has not yet been reported in the literature. Accordingly, the present inventors have found that diaminodiphenylsulfone (DDS) according to the present invention increases muscle mass and effectively restores muscle functions, and thus can be effectively used for the prevention or treatment of a muscle wasting-related disease, thereby completing the present invention.

Technical Solution

An object of the present invention is to provide diaminodiphenylsulfone for preventing or treating a muscle wasting-related disease by increasing muscle mass, preventing muscle loss and effectively restoring muscle functions.

Advantageous Effects

Diaminodiphenylsulfone (Dapsone; DDS) according to the present invention not only increases muscle mass and prevents muscle loss, but also effectively restores muscle functions. Thus, a pharmaceutical composition comprising the same can be effectively used for the prevention or treatment of a muscle wasting-related disease.

BEST MODE

The present invention provides a pharmaceutical composition for preventing or treating a muscle wasting-related disease comprising diaminodiphenylsulfone or a pharmaceutically acceptable salt thereof.

As used herein, the term "diaminodiphenylsulfone" refers to a compound, which is represented by the following formula I and has a generic name of Dapsone or a nickname of DDS. The diaminodiphenylsulfone is a white, odorless and crystalline powder which is a water-insoluble compound. Generally, diaminodiphenylsulfone is administered at a dose of 100 mg/day for the treatment of leprosy. In addition, it is also used for the treatment of dermatitis, rheumatoid arthritis or malaria.

Formula 1

The DDS that is used in the present invention may be commercially available, or may be synthesized or extracted from natural materials, but is not limited thereto. Preferably, the DDS that is used in the present invention may be the one autoclaved after mixing with water in order to further improve the water-insoluble property thereof. The autoclaving may be performed according to a general method known in the art. Preferably, the autoclaving may be performed at a temperature of 121° C. and a pressure of 151 psi for 15-20 minutes.

In a specific example of the present invention, it was found that, when DDS was mixed with water and autoclaved, DDS could be dissolved at a desired concentration in spite of its water-insoluble property and showed a suitable range of effective blood concentration when it was administered to mice. In addition, the results of an antibacterial activity test indicated that the activity of DDS was conserved by autoclaving.

As used herein, the term "pharmaceutically acceptable salt" refers to a formulation of a compound that does not cause significant irritation to an organism to which it is administered and does not abrogate the biological activity and properties of the compound. The pharmaceutical salts include acid addition salts formed by acids that form non-toxic acid addition salts containing a pharmaceutically acceptable anion, for example, inorganic acids such as hydrochloric acid, sulfuric acid, nitric acid, phosphoric acid, hydrobromic acid, hydroiodic acid, and the like, organocarbonic acid such as tartaric acid, formic acid, citric acid, acetic acid, trichloroacetic acid, trifluoroacetic acid, gluconic acid, benzoic acid, lactic acid, fumaric acid, maleic acid, salylic acid and the like, and sulfonic acid such as methanesulfonic acid, ethanesulfonic acid, benzenesulfonic acid, p-toluenesulfonic acid and the like. For example, pharmaceutically acceptable carboxylic acid salts include a metal salt or alkaline earth metal salt formed by lithium, sodium, potassium, calcium, magnesium and the like, salts of amino acids such as lysine, arginine, guanidine and the like, and organic salts such as dicyclohexylamine, N-methyl-D-glucamine, tris(hydroxymethyl)methylamine, diethanolamine, choline, triethylamine and the like, etc.

As used herein, the term "muscle wasting-related disease" refers to a disease or condition that involves symptoms such as the gradual loss of muscle mass. The muscle wasting may be attributed to various causes, including genetic predispositions; age-related diseases such as hypertension, impaired glucose tolerance, diabetes, obesity, dyslipidemia, atherosclerosis, and cardiovascular diseases; chronic diseases such as cancers, autoimmune diseases, infectious diseases, AIDS, chronic inflammatory diseases, arthritis, malnutrition, renal diseases, chronic obstructive pulmonary disease, pulmonary emphysema, rachitis, chronic lower spine pain, peripheral nerve injury, central nerve injury, and chemical injury; conditions such as long-term immobilization, ineffectualness-like conditions such as bone fracture or trauma, and post-surgery bed rest; and the progressive decrease in skeletal muscle mass and strength caused by aging processes. The muscle wasting-related disease can cause weakened physical conditions, which can deteriorate health conditions and induce incapable physical activity.

Preferably, the composition of the present invention can be used for the prevention or treatment of sarcopenia. Specifically, the term "sarcopenia" in the present invention means the gradual decrease in skeletal muscle mass caused by aging, which can directly cause a decrease in muscle strength, resulting in a decrease and impairment in various physical functions.

Preferably, the pharmaceutical composition of the present invention is characterized by increasing muscle mass or preventing muscle loss.

In a specific example of the present invention, it was found that, when DDS of the present invention was administered to mice, the muscle weights of various muscle types (SOL, EDL, GA, and TA) increased, and the response of SOL and EDL to twitch stimulation and tetanic stimulation increased. In addition, it was found that the blood creatine kinase level decreased and the grip strength increased. This suggests that DDS effectively restores and improve muscle function by increasing muscle mass and preventing muscle loss.

As used herein, the term "preventing" refers to all actions that inhibit a muscle wasting-related disease or delay the development of the disease by administering the composition of the present invention.

As used herein, the term "treating" refers to all actions that alleviate or beneficially change the condition of a muscle wasting-related disease by administering the composition of the present invention.

For administration, the pharmaceutical composition of the present invention may comprise, in addition to the DDS or a pharmaceutically acceptable salt thereof, a pharmaceutically acceptable carrier, excipient or diluent. Examples of the carrier, excipient or diluent that may be used in the present invention include lactose, dextrose, sucrose, sorbitol, mannitol, xylitol, erythritol, maltitol, starch, acacia senegal gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, mineral oil, etc.

The pharmaceutical composition of the present invention may be formulated as oral dosage forms such as powders, granules, tablets, capsules, suspensions, emulsions, syrups or aerosol formulations, external dosage forms, suppositories, or sterile injectable solutions. Specifically, the composition of the present invention may be formulated with commonly used diluents or excipients, such as fillers, extenders, binders, wetting agents, disintegrants, surfactants, etc. Solid formulations for oral administration include, but are not limited to, tablets, pills, powders, granules, capsules and the like. Such solid formulations may comprise at least one excipient, for example, starch, calcium carbonate, sucrose, lactose or gelatin. In addition to simple excipients, lubricants such as magnesium stearate or talc may also be used. Liquid formulations for oral administration may contain various excipients, for example, wetting agents, flavoring agents, aromatics and preservatives, other than simple diluents, in addition to water and liquid paraffin. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, Witepsol, Macrogol, Tween 61, cacao butter, laurin fat, glycerogelatin and the like can be used.

The composition of the present invention may be administered orally or parenterally (e.g., intravenously, subcutaneously, intraperitoneally or topically) according to the intended use. The dose of the composition of the present invention may vary depending on the patient's condition and bodyweight, the severity of the disease, the form of drug, and the route and time of administration and can be suitably determined by those skilled in the art.

The present invention also provides a health functional food composition for preventing or ameliorating a muscle wasting-related disease comprising diaminodiphenylsulfone or a pharmaceutically acceptable salt thereof. That is, the composition of the present invention may be administered individually or in combination with other therapeutic agents before or after the development of a muscle wasting-related disease in order to prevent or ameliorate the muscle wasting-related disease.

Preferably, the composition of the present invention may be used for the prevention or amelioration of sarcopenia.

Preferably, the health functional food composition is characterized by increasing muscle mass or preventing muscle loss.

Preferably, the DDS may be autoclaved after mixing with water in order to further improve the water-insoluble property thereof before it is used. The autoclaving may be performed according to a general method known in the art. Preferably, the autoclaving may be performed at a temperature of 121° C. and a pressure of 151 psi for 15-20 minutes.

As used herein, the term "ameliorating" refers to all actions that at least reduce a parameter related to the conditions to be treated, for example, the degree of symptom.

When the health functional food composition of the present invention is used as a food additive, the composition can be added alone or in combination with other foods or food ingredients, and may be used appropriately according to conventional methods. Generally, for the preparation of a food or a beverage, the composition of the present invention is added in an amount of 15 wt % or less, and preferably 10 wt % or less, based on the total weight of the food or beverage. However, for prolonged intake intended for the purpose of health and hygiene or for health control, the amount of the composition may be smaller than the lower limit of the above-specified range. Also, the amount of the used active ingredient can be greater than the upper limit of the above-specified range because there is no problem in the aspect of safety.

There is no particular limit to the kind of food. Examples of foods to which the composition of the present invention can be added include meats, sausages, bread, chocolate, candies, snack, confectionery, pizza, ramen, other noodles, gum, dairy products including ice cream, various soups, beverages, teas, drinks, alcoholic beverages and multi-vitamin preparations. The foods include all health foods in a conventional sense.

The health beverage composition of the present invention may additionally contain various sweetening agents or natural carbohydrates as in conventional beverages. The natural carbohydrates include monosaccharides, such as glucose and fructose, disaccharides, such as maltose and sucrose, natural sweeteners, such as dextrin and cyclodextrin, and synthetic sweeteners, such as saccharin and aspartame, may be used. The amount of the natural carbohydrates in the beverage composition can be suitably selected by a person skilled in the art.

In addition, the composition of the present invention may contain various nutrients, vitamins, electrolytes, flavoring agents, colorants, pectic acid or its salt, alginic acid or its salt, organic acids, protective colloidal thickeners, pH adjusters, stabilizers, preservatives, glycerin, alcohol, carbonating agents used in carbonated drinks, etc. Additionally, the composition of the present invention may contain fruit flesh for the preparation of natural fruit juices, fruit juice beverages and vegetable juices. These components may be used alone or in combination. The contents of these additives in the composition can be suitably selected by a person skilled in the art.

The present invention also provides a method for preventing or treating a muscle wasting-related disease comprising administering a pharmaceutically effective amount of the composition, which comprises diaminodiphenylsulfone or a pharmaceutically acceptable salt thereof, to a subject having a muscle wasting-related disease or being at risk of developing the same.

Preferably, the above method can be achieved by increasing muscle mass or preventing muscle loss.

As used herein, the term "subject" refers to all animals, including humans, who already have a muscle wasting-related disease or are at risk of developing the same. The muscle wasting-related disease can be effectively prevented and treated by administering the composition of the present invention to the subject.

The pharmaceutical composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level of the composition may be determined depending on the subject's type, the disease severity, the subject's age and sex, the type of the muscle wasting-related disease, the activity of the drug, sensitivity to the drug, the time of administration, the route of administration, excretion rate, the duration of treatment, factors including drugs used in combination with the composition, and other factors known in the medical field. The pharmaceutical composition of the present invention may be administered individually or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this amount can be easily determined by a person skilled in the art.

[Mode for Invention]

Hereinafter, the present invention will be described in further detail with reference to examples. It is to be understood, however, that these examples are provided for illustrative purposes only and are not intended to limit the scope of the present invention.

EXAMPLE 1

Preparation of Experimental Animals and DDS 1-1: Experimental Animals 5, 15, 20 and 27-month-old male and female C57BL/6J mice (12 males and 12 females for each age) were purchased from the Korea Research Institute of Bioscience and Biotechnology. The mice were acclimated for 1 week, housed at a temperature of 21±1° C. and a humidity of 60%, and allowed ad libitum access to feed. All the animal studies were approved by the Animal Research Ethical Committee of Seoul National University.

1-2: Administration of DDS and HPLC Analysis of DDS

Because DDS is not easily soluble in water, it was mixed with water and autoclaved, so that it was dissolved to a concentration of 2 mg/kg that is a recommended concentration for human Hansen's disease. The solution was administered to each of the male and female mice. In order to examine whether the administered DDS was successfully absorbed into the blood of the mice, the blood was analyzed by HPLC.

In order to prepare the blood sample, 37.5 µl of glutathione solution (5 mg/mL, water:methanol=1:10) was added to 0.25 mL of EDTA plasma. Then, 5.0 µl of 1 mg/mL diazoxide solution was added thereto, and 0.5 mL of acetone was added, after which the resulting solution was centrifuged at 2700 g for 2 minutes. Then, the solution was evaporated, and the residue was dissolved in 60 µl of HPLC eluent and acetone (18:5 v/v) to prepare a sample for injection into HPLC. The measurement of DDS by HPLC was performed using Water 515 HPLC pump, a Waters 717 plus autosampler, and Waters 996 Photo Diode Array Detector, and the results of the measurement were analyzed using Millenium32 (version 3.05) chromatographic data system (Waters, Etten-Leur, The Netherlands). The column used was C18 (Zwijndrecht, The Netherlands). To isolate and analyze DDS, an eluent of water: acetonitrile:glacial acetic acid:triethylamine (80:20:1.0:0.05, by volume) was used, and the absorbance at 295 nm was measured. The results of the measurement are shown in FIG. 1.

Figure 1:
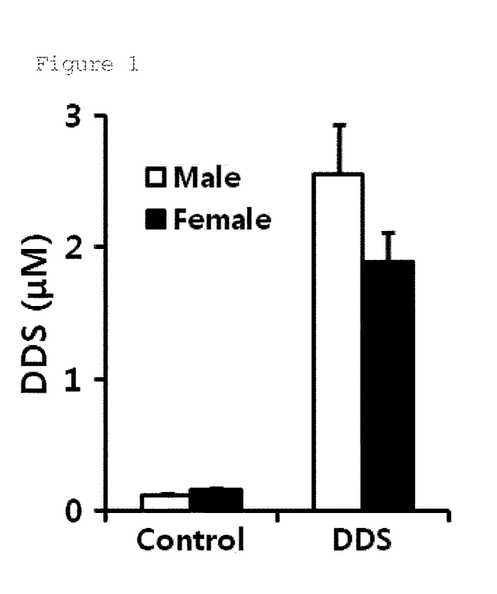
FIG. 1 shows the results of an HPLC analysis of DDS concentration in the blood of mice according to an example of the present invention.

As a result, as can be seen in FIG. 1, DDS was absorbed into the mouse blood at a concentration of 2-3 μM.

1-3: Examination of Activity of Autoclaved DDS

In order to examine whether the treatment of DDS by autoclaving influences the inhibition of activity of DDS, the bacterial growth inhibitory activity of DDS known as an antibiotic was measured.

Figure 2:
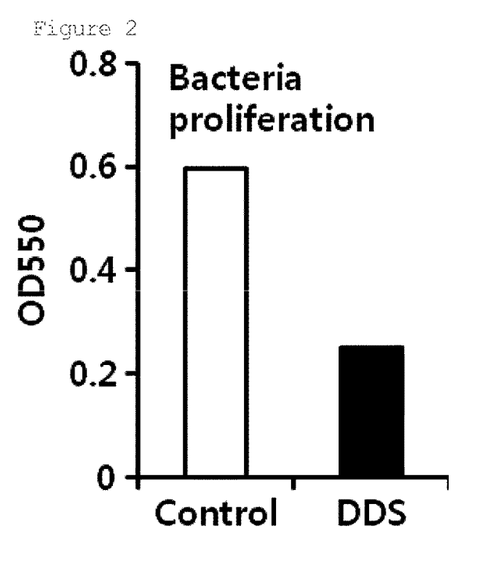
FIG. 2 shows the results of testing the antibacterial activity of DDS according to an example of the present invention.

Specifically, DDS was added to a bacterial medium and autoclaved, and then compared with a control. As a result, as shown in FIG. 2, the bacterial growth inhibitory activity of DDS was maintained.

In addition, in order to examine whether the administration of autoclaved DDS increases water intake, DDS was mixed with water to a concentration of 2 mg/kg, a recommended concentration for human use, and autoclaved, and the resulting solution was administered to 5-month-old, 15-month-old, 20-month-old and 27-month-old male and female mice (12 males and 12 females for each age) at 4-day intervals for 3 months. As a comparative group, the water intake of the mice was measured under the same conditions except for administration of Clenbuterol instead of DDS, and the results of the measurement are shown in FIG. 3.

Figure 3:
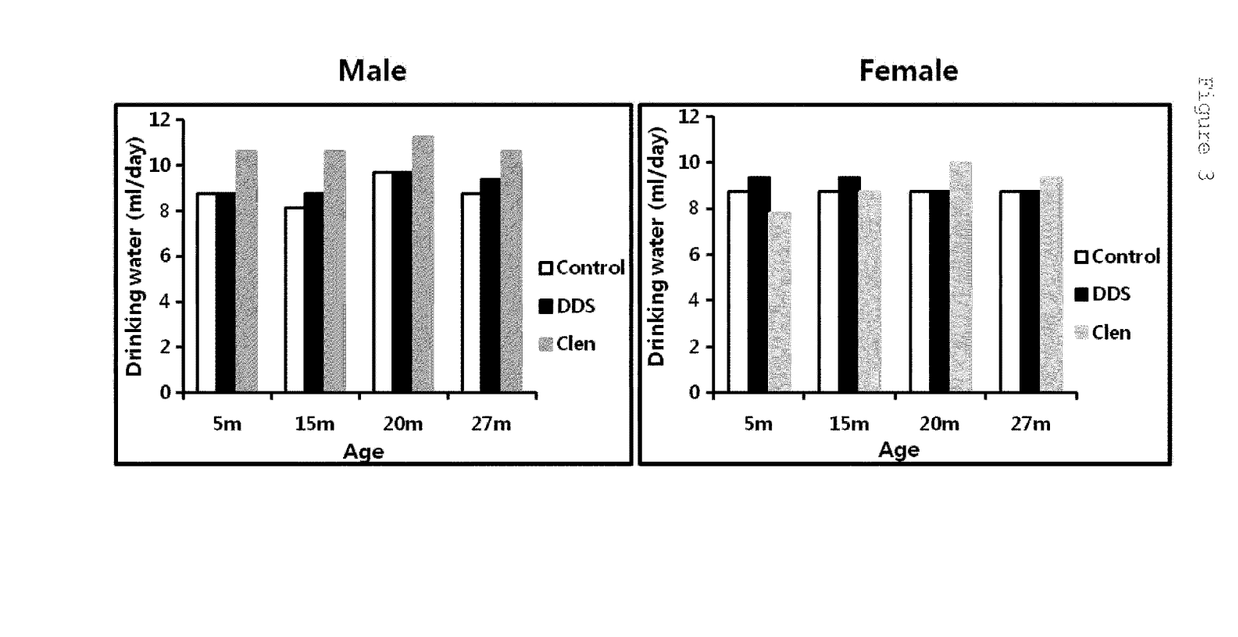
FIG. 3 shows the results of analyzing water intakes caused by the administration of DDS according to an example of the present invention.

As a result, as can be seen in FIG. 3, the water intake of the male and female mice administered with DDS did not significantly differ from that of the control group. However, in the case of the mice administered with Clenbuterol, the water intake of the male mice increased.

EXAMPLE 2

Measurement of Blood Creatine Kinase (CK) Level

In order to examine whether the creatine kinase level known to increase in muscle contraction, muscle injury and sarcopenia caused by aging is controlled by the administration of DDS, the level of creatine kinase in the mouse blood was measured.

Figure 4:
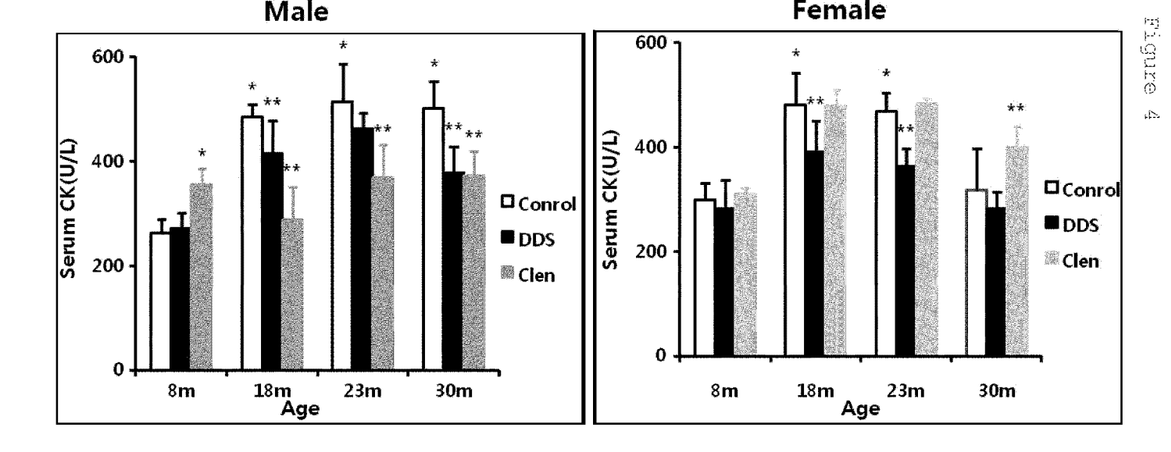
FIG. 4 shows the results of analyzing CK concentration in the blood of mice according to an example of the present invention.

DDS was mixed with water to a concentration of 2 mg/kg, a recommended concentration for human use, and autoclaved, and the resulting solution was administered to 5-month-old, 15-month-old, 20-month-old and 27-month-old male and female mice (12 males and 12 females for each age) at 4-day intervals for 3 months. The mouse blood whose creatine kinase level was to be measured was not hemolytic, and the measurement of the creatine kinase level was performed using EnzyChrom™ Creatine Kinase Assay Kit (ECPK-100, BioAssay Systems) according to the manufacturer's instruction. The measurement of creatine kinase was calculated using the following equation, and the results of the calculation are shown in FIG. 4. As a negative control group, the blood of untreated mice was used, and as a positive control group, the blood of the mice administered with Clenbuterol was used.

$$CK(U/L) = \frac{OD_{40min} - OD_{20min}}{OD_{CALIBRATOR} - OD_{H2O}} \times 150$$

As can be seen in FIG. 4, in the case of the negative control group, the blood creatine kinase level significantly increased in mice of 18 months old and above. This suggests that, when DDS is administered to mice for 3 months, it effectively decreases the increased creatine kinase level in the 18-month-old or older mice. Particularly, in the case of the female mice, it could be seen that even the positive control Clenbuterol-treated group showed a creatine kinase level equal to or higher than that of the negative control, whereas the administration of DDS significantly reduced the blood creatine kinase level. This suggests that DDS assists in restoring muscle functions by effectively inhibiting the increase in creatine kinase caused by aging.

EXAMPLE 3

Measurement of Grip Strength

Figure 5:
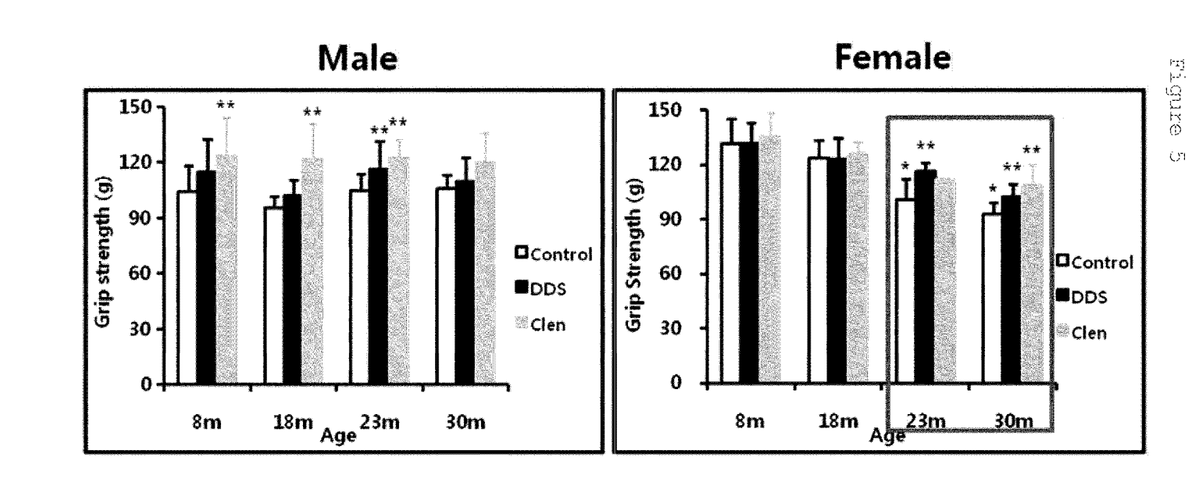
FIG. 5 shows the results of measuring a grip strength of mice according to an example of the present invention.

In order to examine the actual effect of DDS on muscle functions, grip strength was measured. DDS was mixed with water to a concentration of 2 mg/kg, a recommended concentration for human use, and autoclaved, and the autoclaved solution was administered to 5-month-old, 15-month-old, 20-month-old and 27-month-old male and female mice (12 males and 12 females for each age) at 4-day intervals for 3 months. To measure the grip strength of the mice, a grip strength meter (Bioseb) was used. The grip strength of the mice was measured by positioning the mice to grab the grid plate with the forelimbs, slowly pulling the tail in a horizontal direction, and determining the value at the time at which the forelimbs were detached from the grid. For each mice, five measurements were performed and averaged, and the results are shown in FIG. 5. As a negative control group, untreated mice were used, and as a positive control group, mice administered with Clenbuterol were used.

As shown in FIG. 5, in the case of the negative control group, the normal female mice, the grip strength showed a tendency to significantly decrease with aging. In the 18-month-old or younger female mice, the effect of DDS was not distinct, but in the 23-month-old or older female mice, the grip strength of the mice administered with DDS was significantly restored. In the case of the male mice, the decrease in grip strength with aging was not greater than that of the female mice, but the administration of DDS increased the grip strength of the male mice.

EXAMPLE 4

Separation of Mouse Muscle and Measurement of Change in Muscle Weight

Figure 6:
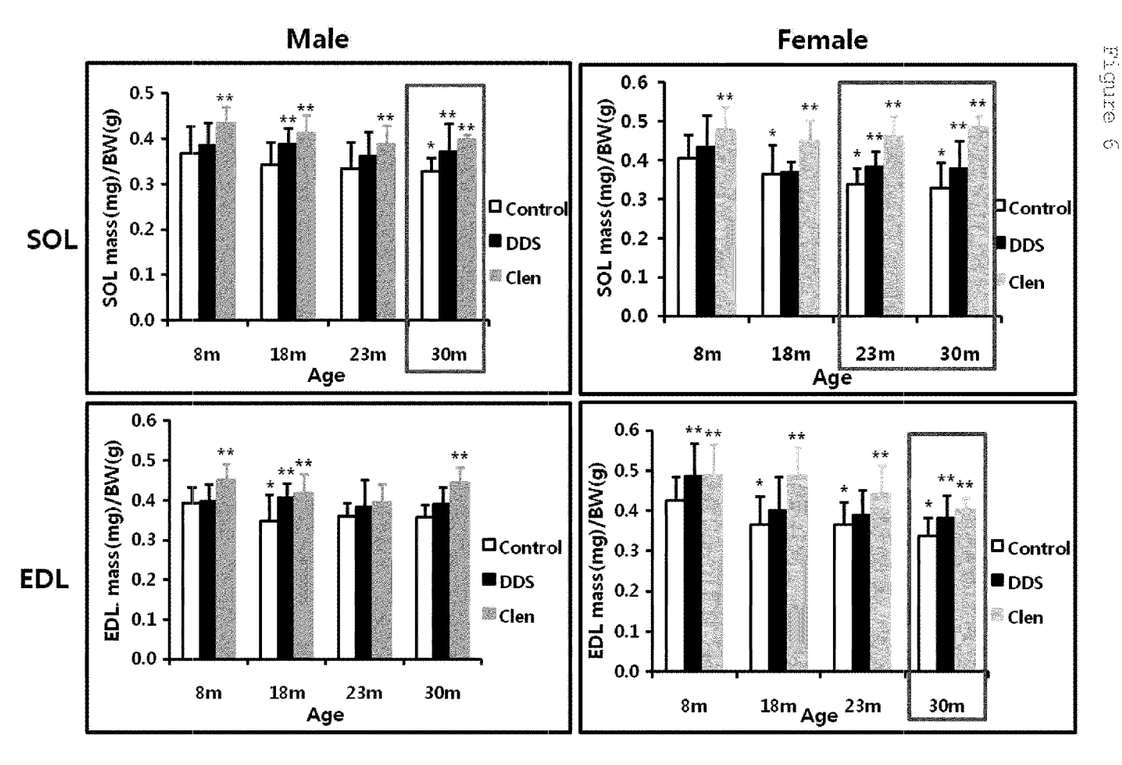
FIG. 6 shows the results of measuring the weight of SOL and EDL according to an example of the present invention.

DDS was mixed with water to a concentration of 2 mg/kg, a recommended concentration for human use, and autoclaved, and the autoclaved solution was administered to 5-month-old, 15-month-old, 20-month-old and 27-month-old male and female mice (12 males and 12 females for each age) at 4-day intervals for 3 months. In order to separate muscle from the mice, the mice were anesthetized by injection with sodium pentobarbital (100 mg/kg body weight). One soleus (SOL) and one extensor digitorum longus (EDL) were carefully separated from the hindlimb of each mouse, so that the muscle was not damaged, and the weight of each of the separated muscles was measured. The results of the measurement are shown in FIG. 6. As a negative control group, the hindlimb of mice not treated with DDS was used, and as a positive control group, the hindlimb muscle of mice administered with Clenbuterol was used.

As can be seen from the graphs in FIG. 6, the weights of SOL and EDL significantly decreased with the aging of the mice. In the mice administered with DDS for 3 months, it was observed that the decrease in muscle mass with aging was inhibited. Particularly, it could be seen that, in the aged mice (i.e., 23-month-old and 30-month-old mice), the weights of SOL and EDL in both female and male mice were restored.

EXAMPLE 5

Separation of Mouse Muscle and Measurement of Change in Muscle Weight

Figure 7:
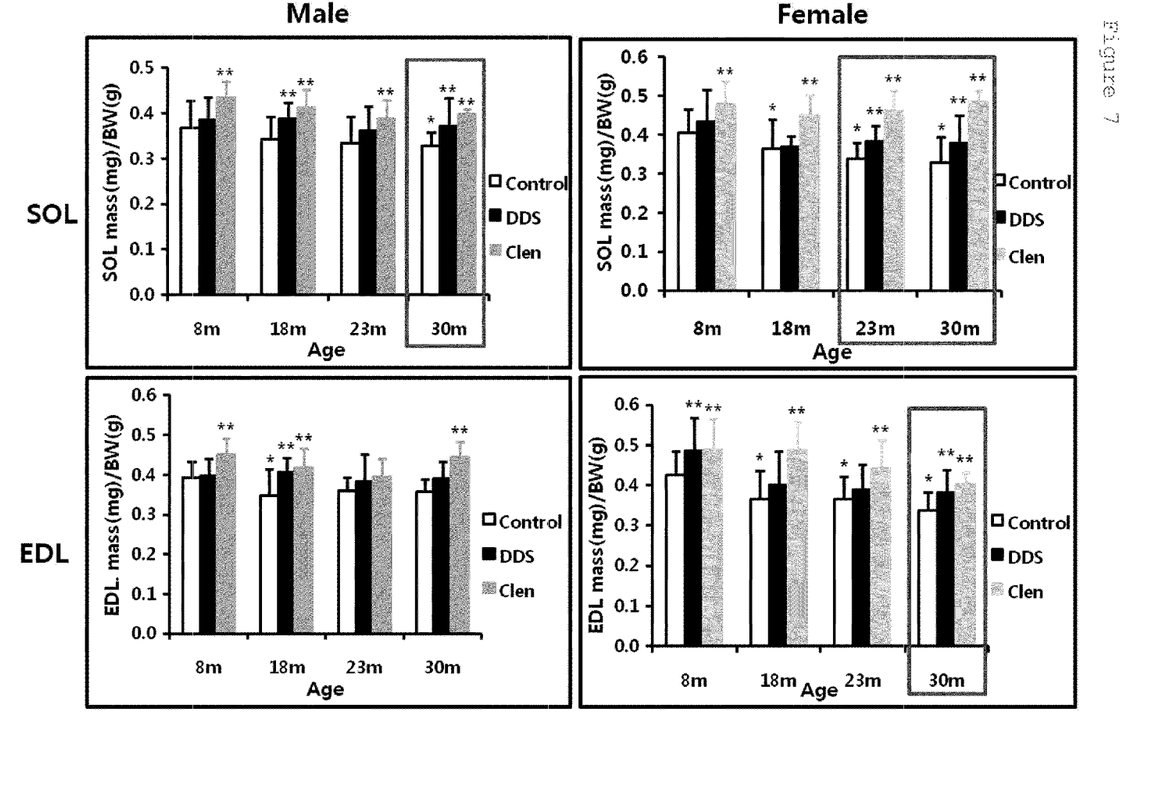
FIG. 7 shows the results of measuring the weight of GA and TA according to an example of the present invention.

DDS was mixed with water to a concentration of 2 mg/kg, a recommended concentration for human use, and autoclaved, and the autoclaved solution was administered to 5-month-old, 15-month-old, 20-month-old and 27-month-old male and female mice (12 males and 12 females for each age) at 4-day intervals for 3 months. In order to separate muscle from the mice, the mice were anesthetized by injection with sodium pentobarbital (100 mg/kg bodyweight). One gastrocnemius (GA) and one tibialis anterior (TA) were carefully separated from the hindlimb of each mouse, so that the muscle was not damaged, and the weight of each of the separated muscles was measured. The results of the measurement are shown in FIG. 7. As a negative control group, the hindlimb of mice not treated with DDS was used, and as a positive control group, the hindlimb muscle of mice administered with Clenbuterol was used.

As can be seen from the graphs in FIG. 7, the weights of GA and TA significantly decreased with the aging of the mice. In the mice administered with DDS for 3 months, it was observed that the decrease in muscle mass with aging was inhibited. Particularly, it could be seen that, in the aged mice (i.e., 23-month-old and 30-month-old mice), the weights of GA and TA in both female and male mice were restored.

EXAMPLE 6

Measurement of Twitch Isometric Force

In order to examine whether DDS has an effect on twitching when electric stimulation is applied to muscle, a system for simultaneously stimulating four muscle tissues was constructed, and the isometric force of muscle was measured using the system.

Figure 8:
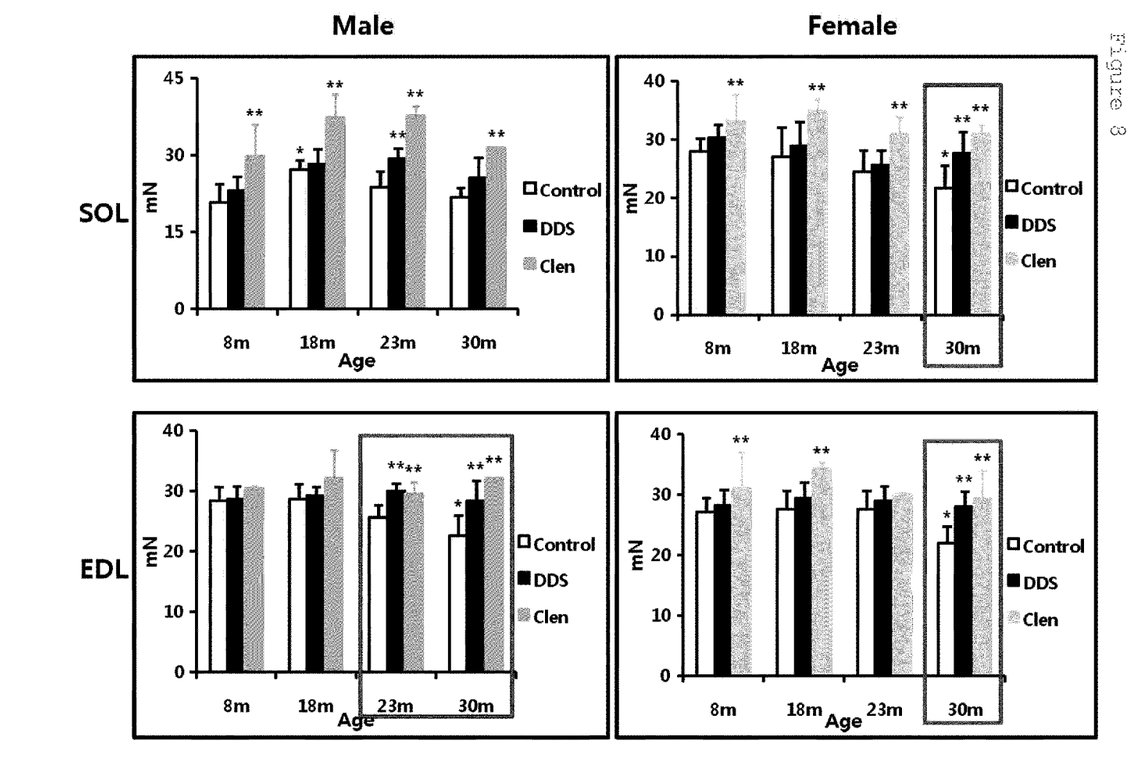
FIG. 8 shows the results of muscle twitch stimulations according to an example of the present invention.

Specifically, mouse muscles (SOL and EDL) were separated in the same manner as described in Example 4, and then the muscle tissues were set and stabilized in oxygen-treated Ringer's solution (25° C., 118 mM NaCl, 4.75 mM KCl, 2.5 mM $CaCl_2$, 1.18 mM $MgSO_4$, 1.18 mM $NaH_2PO4$, 24.8 mM $NaHCO_3$, 10 mM glucose, 0.02 g/L tubocurarine chloride, pH 7.4). One end of the tendons was anchored to a tissue bath, which was filled with Ringer's solution and to which oxygen was smoothly supplied, and the other end was anchored to a FT03 isometric force transducer (Grass instruments, West Warwick, USA). The twitch and tetanus of the muscle were adjusted by the intensity of electric stimulation. The muscle was stabilized in Ringer's solution for 10 minutes, and then an experiment for muscle contraction function was carried out. To maximize the function of the muscle, the length of the muscle showing the highest response at 0.2 Hz (100V), twitch stimulation, was measured and assigned as Lo. Herein, the muscle contraction force (mN) was used as the twitch, and the results of the measurement are shown in FIG. 8. As a negative control group, the hindlimb of mice not treated with DDS was used, and as a positive control group, the hindlimb muscle of mice administered with Clenbuterol was used.

As a result, as can be seen in FIG. 8, the response of the muscle to twitch stimulation decreased with aging, and particularly, more significantly decreased in the 30-month-old mice in which sarcopenia surely occurred. However, in the mice administered with DDS, it could be observed that the reduced muscle twitch force was effectively restored.

EXAMPLE 7

Measurement of Tetanus Isometric Force

In order to examine whether DDS has an effect on tetanizing when electric stimulation is applied to muscle, a system for simultaneously stimulating four muscle tissues was constructed, and the isometric force of muscle was measured using the system.

In the muscle contraction stimulation system, SOL muscle formed the peak plateau under the conditions of 150 Hz, 100 V and 800 ms. That is, the muscle contraction graph showed a tendency to stabilize. On the other hand, EDL muscle showed graph stabilization under the conditions of 100 Hz, 100 V and 400 ms. In this Example, the mice used in Example 6 were used. The mice were rested for a sufficient time after twitch stimulation, and then tetanic stimulation was applied to the mice. As stimulation at the time of formation of a stable graph in which the peak forms the plateau, 150 Hz (100V, 800 ms stimulation time) was used for Soleus, and 100 Hz (100V, 400 ms stimulation time) was used for EDL. Each of these values was used as the peak Isometric force for each muscle, and the results are plotted in unit of mN and shown in FIG. 9. As a negative control group, the hindlimb of mice not treated with DDS was used, and as a positive control group, the hindlimb muscle of mice administered with Clenbuterol was used.

Figure 9:
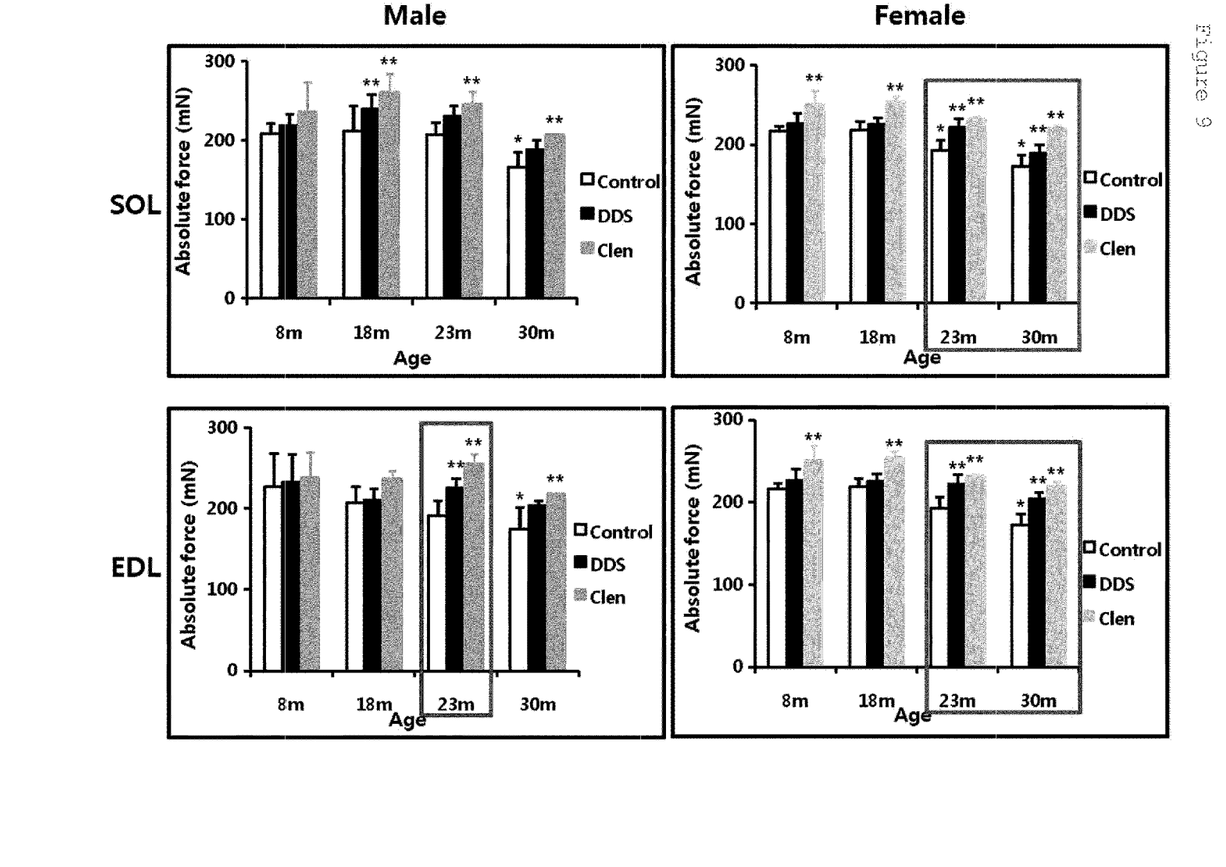
FIG. 9 shows the results of muscle tetanic stimulations according to an example of the present invention.

As a result, as can be seen in FIG. 9, the response of the muscle to tetanic stimulation decreased with aging, like the case of twitch stimulation. Particularly, it could be seen that the response of the muscle more significantly decreased in the 30-month-old mice in which sarcopenia surely occurred. However, in the mice administered with DDS, it could be observed that the reduced muscle tetanic force was effectively restored.

The invention claimed is:

1. A method for treating muscle wasting in an animal, the method comprising administering to the animal suffering from muscle wasting a pharmaceutical composition comprising diaminodiphenylsulfone or a pharmaceutically acceptable salt thereof.

2. A method of treating sarcopenia in an animal, the method comprising administering to the animal a pharmaceutical composition comprising diaminodiphenylsulfone or a pharmaceutically acceptable salt thereof.

3. The method of claim 1, wherein administering the pharmaceutical composition treats muscle wasting in the animal by improving muscle function, increasing muscle mass, or preventing further muscle loss in the animal.

4. The method of claim 1, wherein the diaminodiphenylsulfone or pharmaceutically acceptable salt thereof has been autoclaved at a pressure of 151 psi.

5. The method of claim 1, wherein the animal is a human.

6. The method of claim 1, wherein the muscle wasting is caused by a genetic disposition, age-related disease, chronic disease, long-term immobilization, post-surgery bed rest, or aging.

7. The method of claim 1, wherein the muscle wasting is caused by hypertension, impaired glucose tolerance, diabetes, obesity, dyslipidemia, atherosclerosis, or cardiovascular diseases.

8. The method of claim 1, wherein the muscle wasting is caused by cancer, autoimmune disease, infectious disease, AIDS, chronic inflammatory disease, arthritis, malnutrition, renal disease, chronic obstructive pulmonary disease, pulmonary emphysema, rachitis, chronic lower spine pain, peripheral nerve injury, central nerve injury, and chemical injury.

9. The method of claim 1, wherein the muscle wasting is caused by bone fracture or trauma.

10. The method of claim 2, wherein the animal is a human.

* * * * *